US012629451B2

(12) United States Patent
Ou et al.

(10) Patent No.: US 12,629,451 B2
(45) Date of Patent: May 19, 2026

(54) METHOD FOR MANUFACTURING EXTRACELLULAR MATRIX COMPOSITION

(71) Applicant: 3D GLOBAL BIOTECH INC., New Taipei City (TW)

(72) Inventors: Keng-Liang Ou, Taipei City (TW); Hsu-An Pan, Yilan County (TW); En-Kai Chang, New Taipei City (TW)

(73) Assignee: 3D GLOBAL BIOTECH INC., New Taipei City (TW)

( * ) Notice: Subject to any disclaimer, the term of this patent is extended or adjusted under 35 U.S.C. 154(b) by 392 days.

(21) Appl. No.: 18/225,482

(22) Filed: Jul. 24, 2023

(65) Prior Publication Data

US 2024/0335590 A1 Oct. 10, 2024

(30) Foreign Application Priority Data

Apr. 6, 2023 (TW) .................................. 112112766

(51) Int. Cl.
*A61L 27/36* (2006.01)
*C12N 5/00* (2006.01)

(52) U.S. Cl.
CPC ....... *A61L 27/3687* (2013.01); *A61L 27/3633* (2013.01); *C12N 5/0075* (2013.01); *C12N 2531/00* (2013.01); *C12N 2533/74* (2013.01)

(58) Field of Classification Search
None
See application file for complete search history.

(56) References Cited

U.S. PATENT DOCUMENTS

| | | |
|---|---|---|
| 2010/0291219 A1 | 11/2010 | Karp et al. |
| 2021/0008788 A1 | 1/2021 | Murphy et al. |
| 2021/0238329 A1 | 8/2021 | Suzuki et al. |
| 2022/0002704 A1 | 1/2022 | Satoh et al. |
| 2023/0018016 A1 | 1/2023 | Chang |
| 2023/0093822 A1 | 3/2023 | Suzuki et al. |

FOREIGN PATENT DOCUMENTS

| | | |
|---|---|---|
| CN | 113614179 A | 11/2021 |
| CN | 115135746 A | 9/2022 |
| TW | 202024151 A | 7/2020 |
| TW | 202124708 A | 7/2021 |

OTHER PUBLICATIONS

Darling & Smith, "measuring the formaldehyde protein-DNA cross-link reversal rate" Anal Chem (Year: 2014).*
Eydelnant et al, "microgels on demand" Nature Communications (Year: 2014).*
Kadhim et al., "effect of crosslinking agent on the swelling ratio and water retention capacity of polyacrylate and polyvinyl alcohol" Journal of Applied Sciences and Nanotechnology (Year: 2022).*
Kapalczynska et al. "2D and 3D cell cultures—a comparison of different types of cancer cell cultures" Arch Med Sci (Year: 2016).*
Millipore "Microfiltration membranes for the laboratory" (Year: 2009).*
Saldin et al., "extracellular matrix hydrogels from decellularized tissues: structures and function" Acta Biomaterialia (Year: 2017).*
Tomic et al., "Alginate based hydrogels and scaffold for biomedical applications" Mar. 2023.*
Schafer et al., "Ascorbic acid deficiency in cultured human fibroblasts" Journal of Cell Biology (Year: 1967).*

* cited by examiner

*Primary Examiner* — Tracy Vivlemore
*Assistant Examiner* — John David Moore
(74) *Attorney, Agent, or Firm* — Li & Cai Intellectual Property (USA) Office

(57) ABSTRACT

A method for manufacturing an extracellular matrix composition includes providing a gel, carrying out a crosslinking treatment, carrying out a single type cell culture, carrying out a decrosslinking treatment, and carrying out an extraction treatment. The crosslinking treatment includes adding a crosslinking agent to the gel to obtain a crosslinked gel. The cell culture includes implanting cells of a singular type on the crosslinked gel and incubating the cells by adding a culture solution. The decrosslinking treatment includes adding a decrosslinking agent to the crosslinked gel to obtain a decrosslinked mixture that contains an extracellular matrix. The extraction treatment includes filtering the decrosslinked mixture to obtain the extracellular matrix composition that is in a liquid state.

10 Claims, 6 Drawing Sheets

METHOD FOR MANUFACTURING EXTRACELLULAR MATRIX COMPOSITION

CROSS-REFERENCE TO RELATED PATENT APPLICATION

This application claims the benefit of priority to Taiwan Patent Application No. 112112766, filed on Apr. 6, 2023. The entire content of the above identified application is incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to a method for manufacturing a cellular matrix composition, and more particularly to a method for manufacturing a cellular matrix composition that is used in preparing a bio-ink.

BACKGROUND OF THE DISCLOSURE

Extracellular matrix (ECM) is a component synthesized by cells and secreted into the extracellular space, and ECM mainly contains fibers, polysaccharides, proteoglycans, etc. ECM is widely used in the field of biomedical materials to provide structural support to cells and to regulate cell behavior, and facilitate organ formation and tissue regeneration.

In conventional technologies, the method of mass production of ECM includes obtaining a complex mixture of ECM from multiple cells in animal tissues by grinding tissues such as mouse liver. Although this method allows high concentration of ECM to be easily obtained, the source cannot be directly extracted from human organs due to regulatory and ethical reasons. Furthermore, the batch stability of the ECM that is produced cannot be controlled due to the organ tissues containing multiple types of cells and the differences in the composition ratio of the cells, which results in safety risks in clinical applications of products derived from the ECM thus produced. In addition, the batch stability of the ECM cannot be controlled through a single cell source.

In addition, a less commonly used method is to freeze-dry the cell culture for 24 hours after the cells are cultured in a flat petri dish, and then scrape the cell culture off the petri dish by using a spatula to separate the cell culture from the culture dish. Afterwards, the ECM is extracted from the cell culture. However, this method requires a longer processing time due to the process freeze-drying process, and the scraping step generates extremely high wear and tear and is susceptible to human error, which reduces the yield of ECM and requires petri dishes in large quantities and/or having large areas for mass production to be achieved. However, the method is not commercially viable because of the time consuming and costly production processes involved therewith.

Therefore, how to improve the yield of the cellular matrix composition through improvements in manufacturing methods to overcome the aforementioned problems has become an issue to be addressed in the relevant industry.

SUMMARY OF THE DISCLOSURE

In response to the above-referenced technical inadequacies, the present disclosure provides a method for manufacturing an extracellular matrix composition. The method includes providing a gel, carrying out a crosslinking treatment, carrying out a single type cell culture, carrying out a decrosslinking treatment, and carrying out an extraction treatment. The crosslinking treatment includes adding a crosslinking agent to the gel to obtain a crosslinked gel. The cell culture includes implanting cells of a singular type on the crosslinked gel and incubating the cells by adding a culture solution. The decrosslinking treatment includes adding a decrosslinking agent to the crosslinked gel to obtain a decrosslinked mixture that contains an extracellular matrix. The extraction treatment includes adding a lysis enzyme to the decrosslinked mixture and filtering the decrosslinked mixture to obtain the extracellular matrix composition that is in a liquid state.

In certain embodiments, the gel is a sodium alginate having a concentration of from 3 vol % to 5 vol %.

In certain embodiments, the gel is a two-dimensional gel or a three-dimensional gel. When the gel is the two-dimensional gel, a height of the two-dimensional gel is from 10 mm to 40 mm. When the gel is the three-dimensional gel, the three-dimensional gel has a micron-sized spherical structure or a laminar printed structure, the micron-sized spherical structure having an average particle size ranging from 0.2 mm to 2 mm.

In certain embodiments, the crosslinking agent is calcium chloride, barium chloride, zinc chloride, calcium carbonate, calcium sulfate, or calcium lactate.

In certain embodiments, the cells are human and animal mesenchymal stem cells, human hepatocellular carcinoma cells, fibroblasts, or epithelial stem cells.

In certain embodiments, the culture solution includes 50 µg/ml to 100 µg/ml of ascorbic acid.

In certain embodiments, the decrosslinking agent is sodium citrate or ethylenediaminetetraacetic acid.

In certain embodiments, before carrying out the decrosslinking treatment, the method further includes a decellularization treatment that includes adding a decellularizing agent.

Therefore, in the method for manufacturing an extracellular matrix composition provided by the present disclosure, by virtue of "the crosslinking treatment including adding a crosslinking agent to the gel to obtain a crosslinked gel," and "the decrosslinking treatment including adding a decrosslinking agent to the crosslinked gel to obtain a decrosslinked mixture that contains an extracellular matrix," the yield of the extracellular matrix composition can be increased.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The described embodiments may be better understood by reference to the following description and the accompanying drawings, in which.

DETAILED DESCRIPTION OF THE EXEMPLARY EMBODIMENTS

Figure 1:
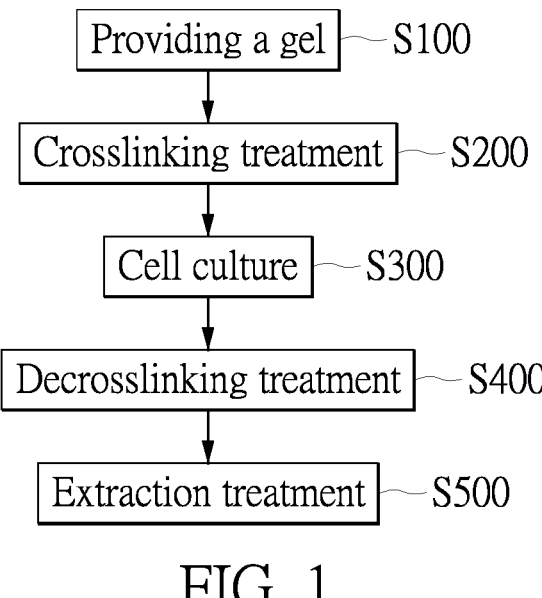
FIG. 1 is a flowchart of a method for manufacturing an extracellular matrix composition according to the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

Embodiments of the present disclosure provide a method for manufacturing an extracellular matrix composition. The method at least includes following steps: S100: providing a gel; S200: carrying out a crosslinking treatment; S300:

carrying out a single type cell culture; S400: carrying out a decrosslinking treatment; and S500: carrying out an extraction treatment.

Specifically, the gel provided in the step S100 can be a sodium alginate having a concentration of from 3 vol % to 5 vol %. When a concentration of the sodium alginate is less than 3 vol %, a gel body formed after crosslinking has insufficient stiffness, and when the concentration of the sodium alginate is greater than 5 vol %, the sodium alginate becomes exceedingly stiff during crosslinking, so that it is difficult for the gel to have a smooth form. Therefore, when the concentration of the sodium alginate is from 3 vol % to 5 vol %, a stable carrying surface for cells can be provided after crosslinking.

Furthermore, a viscosity of the sodium alginate can be from 1 cP to 100 cP for the sodium alginate to be flatly disposed at a bottom of a container. In one embodiment of the present disclosure, a height of the gel is from 10 mm to 40 mm. When the height of the gel is less than 10 mm, the gel may crack during relevant operations, and if the height of the gel is greater than 40 mm, crosslinking reactions may be non-uniformly carried out in the gel.

In one embodiment of the present disclosure, nutritional components, such as vitamins and growth factors that are needed by the cells can be further added to the gel, so as to stimulate cell proliferation and cellular differentiation and increase a growth speed of the cells.

In the step S200 of adding a crosslinking agent to the gel, the gel is changed from an original gel state to a jelly-like solid state to obtain a crosslinked gel. The crosslinking agent is a substance that bonds multiple linear molecules to each other so that the multiple linear molecules are crosslinked into a network structure. In the present disclosure, the crosslinking agent may contain metal ions, and a valence of the metal ions can be more than two. For example, the crosslinking agent may be calcium chloride, barium chloride, zinc chloride, calcium carbonate, calcium sulfate, or calcium lactate. In one preferred embodiment of the present disclosure, the crosslinking agent is from 5 vol % to 25 vol % of a calcium chloride solution, and the crosslinking volume ratio of sodium alginate to calcium chloride can be from 1 to 8.5, so as to achieve a better crosslinking effect.

In addition, a duration for carrying out crosslinking in the step S200 can be from 5 minutes to 10 minutes. If the duration for carrying out crosslinking is less than 5 minutes, only the outside of the gel is cured, thus resulting in incomplete curing. On the other hand, it is not economical for the duration for carrying out crosslinking to be more than 10 minutes. The crosslinking temperature can be from 4° C. to 37° C. After the crosslinking process, the gel is rinsed twice with phosphate buffered saline (PBS) to remove residual crosslinking agent. It should be noted that the state of the cross-linked gel of the present disclosure will not be changed by changes in temperature.

Afterwards, in the step S300, the cells are implanted on the crosslinked gel and incubated with a culture solution. The cells used in this disclosure can be, human and animal mesenchymal stem cells (MSC), human hepatocellular carcinoma cells, fibroblasts, epithelial cells, endothelial cells, or epidermal stem cells. The cell density for implantation is preferably from 51,000 cells/cm$^2$ to 85,000 cells/cm$^2$.

In one embodiment of the present disclosure, the composition of the culture solution may include glycine, L-arginine hydrochloride, L-glutamine, L-isoleucine, L-leucine, L-methionine, L-phenylalanine, L-serine, L-threonine, L-tryptophan, L-valine, choline chloride, calcium pantothenate, niacinamide, pyridoxine hydrochloride, riboflavin, thiamine hydrochloride, and D-glucose.

In one preferred embodiment of the present disclosure, the culture solution can further include 50 μg/ml to 100 μg/ml of an ascorbic acid, so as to increase a growth number of the cells. In other words, a concentration of the ascorbic acid in the culture solution can be from 0.005% to 0.01%.

In one embodiment of the present disclosure, cells are cultured in an environment having 5% to 10% of $CO_2$, and a pH value of from 7.2 to 7.4 for 3 days to 7 days. After the completion of cell culture, the culture solution is removed and the cells are rinsed for one time by using PBS. Before the decrosslinking treatment in the step S400, the cells can undergo decellularization treatment by means of a decellularizing agent to facilitate the preparation of an extracellular matrix composition that is more biocompatible. In the present disclosure, the decellularizing agent may be a mixture of ammonium hydroxide ($NH_4OH$) and a non-ionic surfactant. For example, the non-ionic surfactant may be TRITON™ X-100, dodecyl maltoside, digitonin, tween 20, tween 80, etc.

In one preferred embodiment of the present disclosure, the decellularization treatment can include treating the cells with 20 mM of ammonium hydroxide and 0.5 vol % to 1 vol % of TRITON™ X-100 for 5 minutes to 15 minutes, and rinsing the cells twice with PBS. However, the above examples are only one possible embodiment and are not intended to limit the present disclosure.

Next, in the step S400, a decrosslinking agent is added to the crosslinked gel to obtain a decrosslinked mixture that contains an extracellular matrix. In one embodiment of the present disclosure, the decrosslinking agent may be sodium citrate or ethylenediaminetetraacetic acid. For example, the decrosslinking treatment is adding 0.3 M to 0.6 M of sodium citrate to the crosslinked gel such that a content of sodium citrate is 1.3% to 2.6% of the gel, mixing the gel and sodium citrate for 1 hour to 3 hours, and reacting at 4° C. for 8 hours to 16 hours to complete the decrosslinking treatment of the gel. After the decrosslinking treatment, the gel is a decrosslinked mixture solution that is in a liquid state and contains the extracellular matrix.

Finally, in the step S500, an extraction treatment is carried out on the decrosslinked mixture to obtain the extracellular matrix composition in a liquid state. Specifically, the extraction treatment is performed by filtering the decrosslinked mixture through a filter having a pore size of 0.22 μm. Preferably, a lysis enzyme can be added to the decrosslinked mixture and stirred for 3 hours to 6 hours before the extraction treatment to increase the extraction efficiency. For example, the lysis enzyme can be pepsin or collagenase. The amount of lysis enzyme used is from 0.4% to 1.2% of the decrosslinked mixture. In the present disclosure, the extracellular matrix composition contains 0.12% or more of a total protein concentration of the extracellular matrix.

In one example of the present disclosure, in order to provide a suitable reaction environment for the lysis enzyme, the pH value of the decrosslinked mixture can be adjusted to be from 2 to 4 by adding 1 N to 3 N of hydrochloric acid (HCl). After a lysis treatment is completed, the pH value of the decrosslinked mixture can be adjusted to be from 7 to 8 by adding sodium hydroxide (NaOH) to carry out neutralization reaction. The decrosslinked mixture is then stirred for 1 hour before being filtered.

In one embodiment of the present disclosure, the extraction treatment may include a first extraction treatment and a second extraction treatment. In the first extraction treatment, the decrosslinked mixture is first filtered through a filter having a pore size of 10 μm to obtain a first filtrate. Afterwards, deionized water ($ddH_2O$) is added to the first filtrate and stirred for 10 minutes to 30 minutes, and then the second extraction treatment is carried out. The second extraction treatment is carried out by filtering the first filtrate by using a filter having a pore size of 0.22 μm to obtain an extracellular matrix composition (i.e., a decellularized extracellular matrix gel) having a higher purity. Preferably, the first extraction treatment and the second extraction treatment use negative pressure filtration to increase the efficiency of the extraction treatment.

It should be further noted that, in the step S100, the gel can be provided by a two-dimensional (2D) gel manufacturing process or a three-dimensional (3D) gel manufacturing process. In the 2D gel manufacturing process, the gel is laid flat on the bottom surface of the culture vessel so that the cells do not adhere directly to the bearing surface of the culture vessel. In the 3D gel manufacturing process, the gel can have a micron-sized spherical structure or a laminar printed structure. The 2D gel manufacturing process and the 3D gel manufacturing process are described below in more detail.

Reference is made to FIGS. 2A, 2B, 3, and 4A to 4C. In one embodiment of the present disclosure, a 2D gel manufacturing process is used. Sodium alginate having a concentration of 4 vol % is spread on a petri dish so that a gel layer has a height of 20 mm, calcium chloride having a concentration of 10 vol % is added to carry out crosslinking for 5 minutes, and the gel layer is then rinsed twice with PBS to remove the residual crosslinking agent. Fibroblasts are implanted on the gel layer at a density of 51,000 cells/cm². After 5 days of culturing, the culture solution is removed from the gel layer. The gel layer is then rinsed once with PBS, treated with 20 mM of $NH_4OH$ and 1 vol % of TRITON™ X-100 for 10 minutes, and rinsed twice with PBS. After adding 0.4 M of sodium citrate to the gel layer, the gel layer and the sodium citrate are put into a beaker, mixed for 2 hours and placed at 4° C. for 8 hours to complete the decrosslinking treatment. In the extraction treatment, the pH value of the mixture is adjusted to 2 and then 240 mg of pepsin is added in the beaker and stirred for 3 hours. The pH value of the mixture is then adjusted to 7 and stirred for 1 hour. Afterwards, the mixture is filtered by using a filter having a pore size of 10 μm under negative pressure. Finally, deionized water is added until a volume of the entire mixture is 240 ml and the mixture is then mixed and stirred for 10 minutes, and then the mixture is filtered by using a filter having a pore size of 0.22 μm under negative pressure to obtain the decellularized extracellular matrix (dECM) gel.

A difference between a Comparative Example and embodiments of the present disclosure is that in the Comparative Example, the fibroblasts are directly implanted on the petri dish at a density of 51,000 cells/cm² for cell culture, i.e., the cells directly adhere to the petri dish. After 5 days of culturing, the culture solution is removed from the gel layer. The gel layer is then rinsed once with PBS, treated with 20 mM of $NH_4OH$ and 1 vol % of TRITON™ 100 for 10 minutes, and rinsed twice with PBS. Afterwards, the petri dish is freeze-dried in a freeze-dryer for 24 hours, and then the freeze-dried cell powder is removed from the petri dish by scraping with a spatula for extraction treatment. In the extraction treatment, the pH value of the mixture is adjusted to 2 and 240 mg of pepsin is added and mixed for 3 hours, and then the pH value of the mixture is adjusted to 7 and the mixture is mixed for 1 hour. The mixture is then filtered by using a filter having a pore size of 0.22 μm under negative pressure to obtain the dECM gel.

Figure 2A:
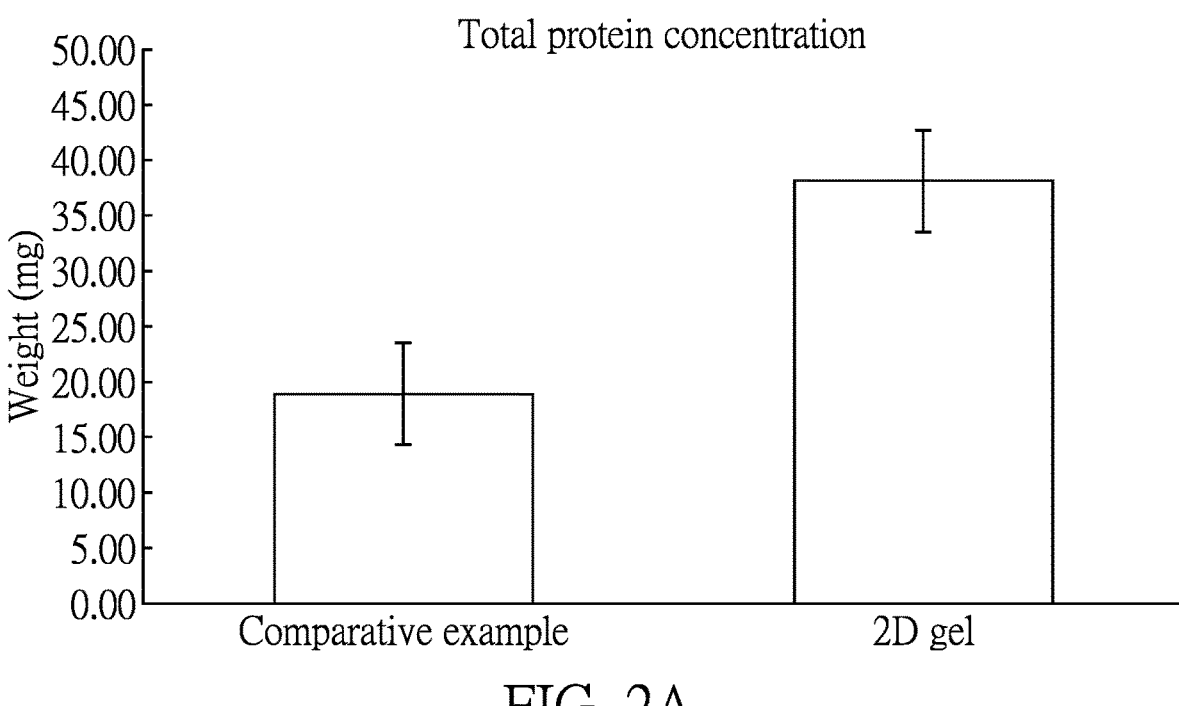
FIG. 2A is a histogram showing differences in total protein concentrations when cell cultures are carried out in different ways.
Figure 2B:
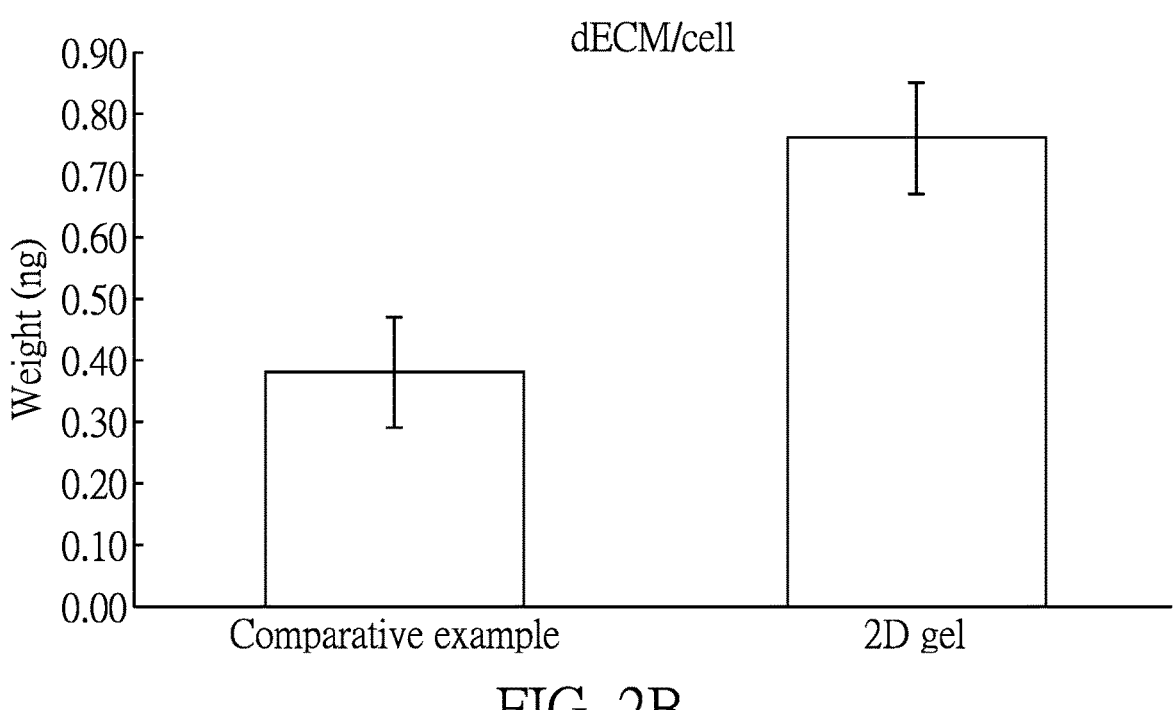
FIG. 2B is a histogram showing differences in weights of dECM/cells when cell cultures are carried out in different ways.

Total protein concentrations of products of the preceding embodiments and the Comparative Example are measured by using the Bio-Rad protein assay kit, and the protein concentrations are further obtained by combining the reagent with the protein and measuring light absorbance value by using colorimetric analysis. As shown in FIG. 2A and FIG. 2B, the total protein concentration of the product in this embodiment of the present disclosure is 38.21±4.65 mg, and is higher than the total protein concentration of 19.00±4.58 mg of the Comparative Example. In addition, for the average amount of dECM produced per cell, after calculation, the average amount of dECM produced per cell in this embodiment of the present disclosure is 0.76±0.09 dECM/cells (ng), which is higher than 0.38±0.09 dECM/cells (ng) as in the Comparative Example. Therefore, in the present disclosure, the method for manufacturing an extracellular matrix composition has higher productivity compared with the conventional method as shown by the Comparative Example.

Figure 3:
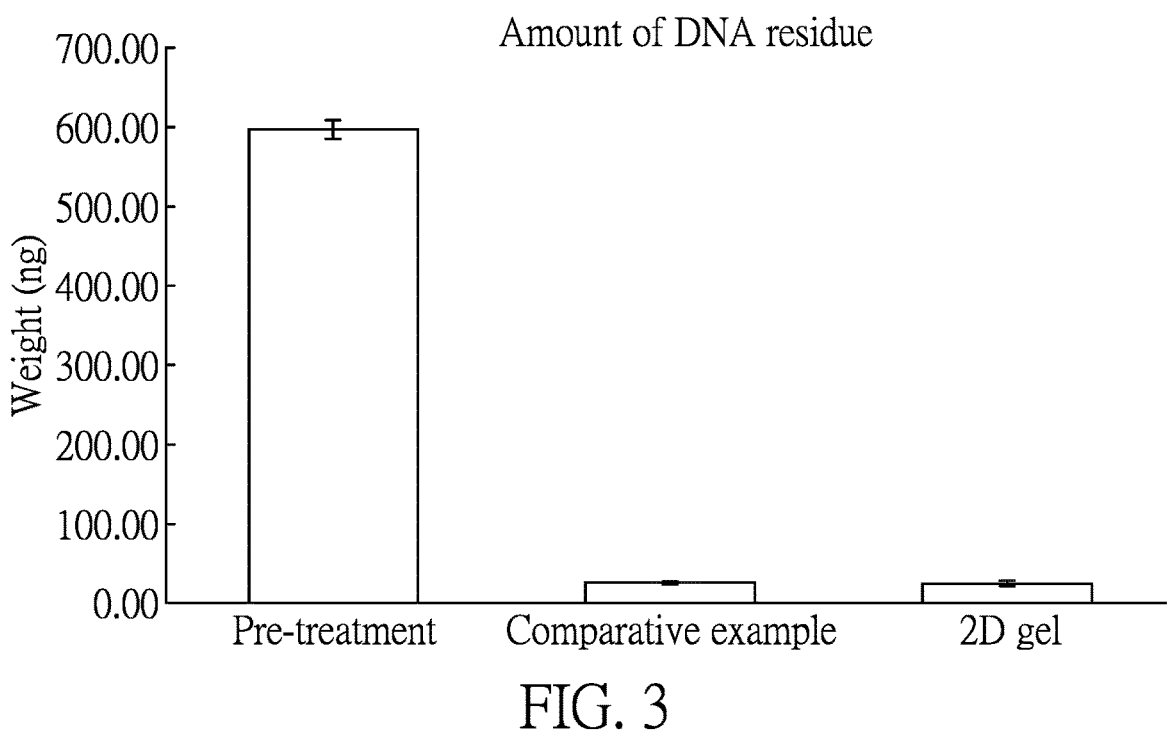
FIG. 3 is a histogram showing differences in DNA residues when cell cultures are carried out in different ways.

Further, as shown in FIG. 3, amounts of DNA residue of the embodiments of the present disclosure and that of the Comparative Example are compared. An amount of DNA residue in the dECM is determined by measuring the absorbance value of samples at a wavelength of 545 nm by using the dsDNA assay kit, and calculating the DNA content. The method for manufacturing an extracellular matrix composition provided in the present disclosure includes a decellularization treatment that provides excellent decellularization while increasing yield, thereby resulting in a finished dECM product having almost no DNA residue.

Figure 4A:
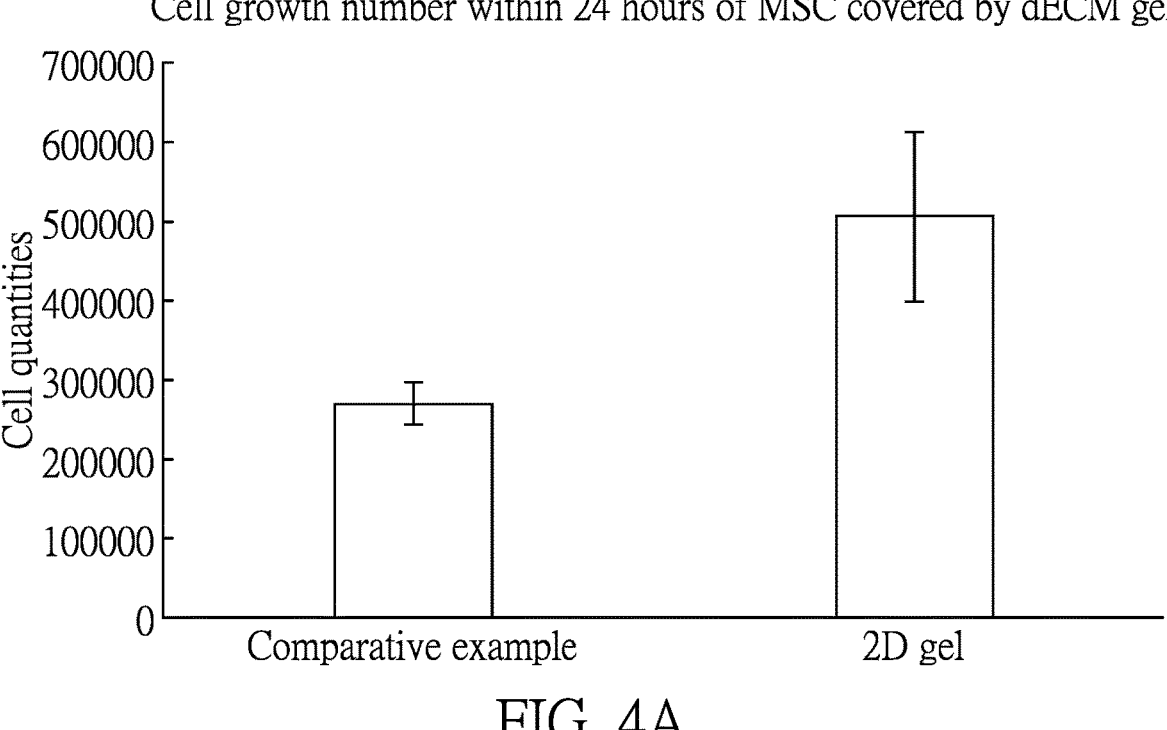
FIG. 4A is a histogram showing differences in cell quantities when cell cultures are carried out in different ways.
Figure 4B:
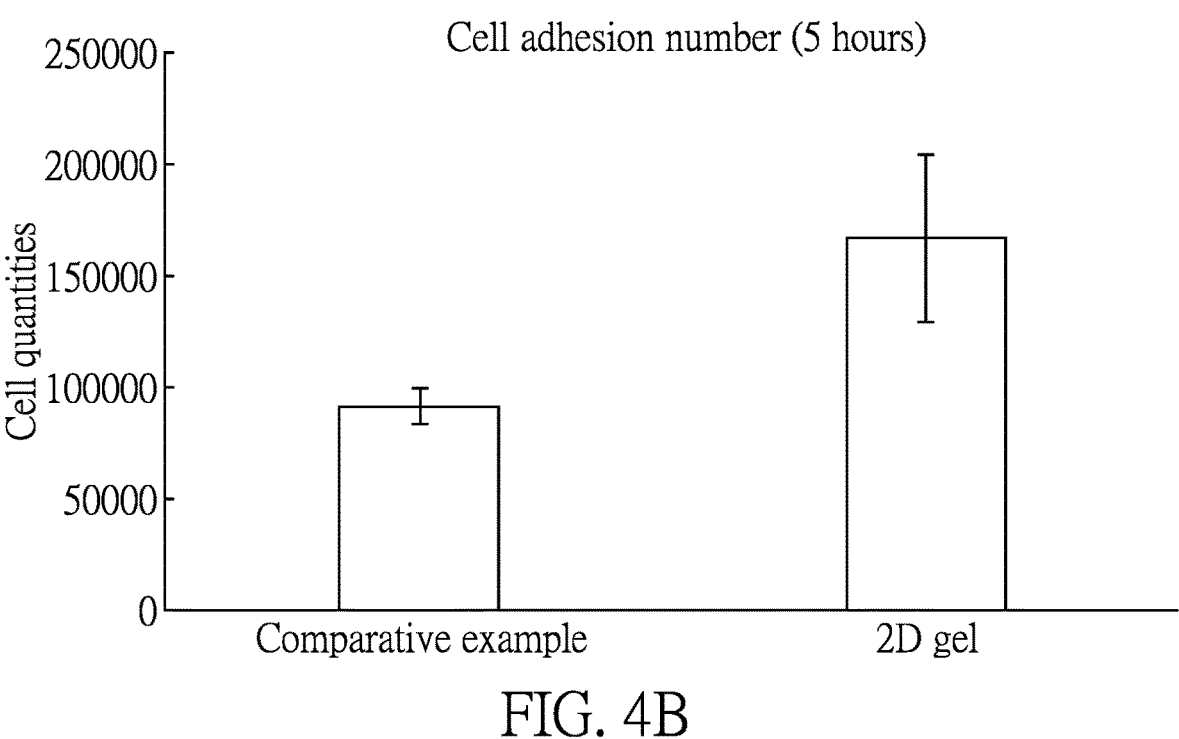
FIG. 4B is a histogram showing differences in cell adhesion numbers when cell cultures are carried out in different ways.
Figure 4C:
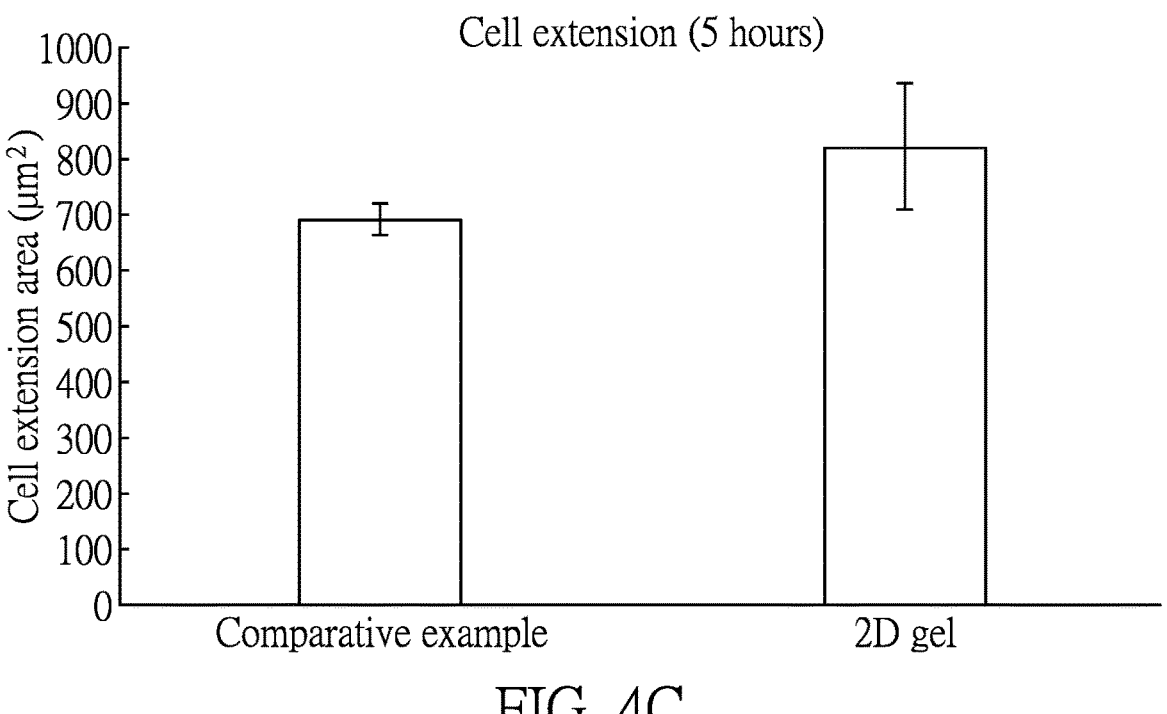
FIG. 4C is a histogram showing differences in cell expansion areas when cell cultures are carried out in different ways.

It should be noted that the use of the dECM gel of the present disclosure in cell culture can contribute to cell growth. As shown in FIG. 4A to FIG. 4C, in petri dishes initially having $2\times10^5$ fibroblasts, equal amounts of dECM gel produced in the 2D gel manufacturing process of the present disclosure and a dECM solution produced in the Comparative Example are respectively added and cultured for 24 hours. As shown in FIG. 4A, in the embodiment in which the dECM gel of the present disclosure is added, the fibroblasts are coated with the dECM gel of the present disclosure, and the cell number is increased by more than two times. In other words, the dECM gel produced in the 2D gel manufacturing process of the present disclosure has a higher concentration, and can assist the cells to proliferate rapidly.

Reference is further made to FIG. 4B and FIG. 4C, in petri dishes initially having $2\times10^5$ fibroblasts, equal amounts of dECM gel produced in the 2D gel manufacturing process of the present disclosure and the dECM solution produced in the Comparative Example are respectively added and cultured for 5 hours to observe cell adhesion and extension. The results in FIG. 4B shows that the cell adhesion number in the embodiment having the dECM gel of the present disclosure is significantly higher than the cell adhesion number in the embodiment having the dECM gel of the Comparative Example, and the dECM gel of the present disclosure stabilizes the adhesion and growth of the cells. Furthermore, the results in FIG. 4C show that, in the embodiment to which the dECM gel of the present disclosure is added, the cells have a larger extension area compared to the cells in the Comparative Example.

In another embodiment of the present disclosure, a 3D gel manufacturing process is used. The 3D gel manufacturing process is substantially the same as the aforementioned 2D gel manufacturing process. A difference between the two manufacturing processes is that, in the 2D gel manufacturing process, the sodium alginate is spread on the petri dish carrier surface; in one embodiment of the 3D gel manufacturing process, the gel can have a micron-sized spherical structure, and the size of the micron-sized spherical structure. The average particle size of the micron-sized spherical structure can range from 0.2 mm to 2 mm, preferably from 0.4 mm to 1.5 mm, and the particle size of each micron-sized spherical structure can be different, so as to improve the cell culture volume. In another embodiment of the 3D gel manufacturing process, the gel may have a laminar printed structure. However, the above examples are only one possible embodiment and are not intended to limit the scope of the present disclosure.

Figure 5A:
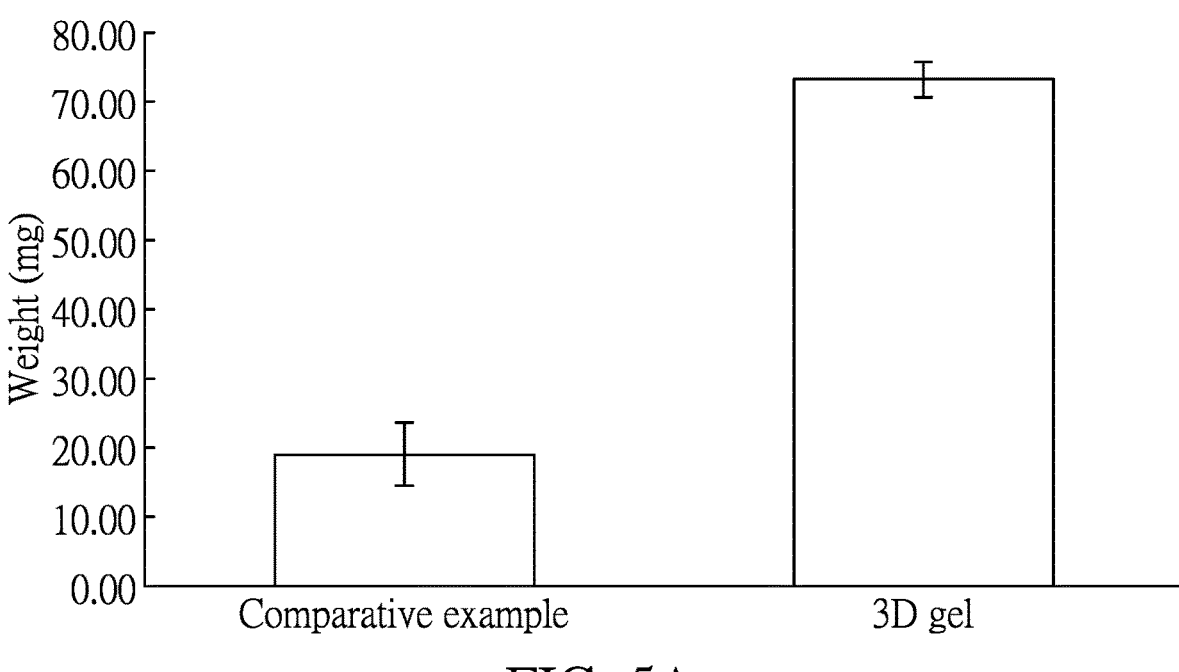
FIG. 5A is another histogram showing differences in total protein concentrations when cell cultures are carried out in different ways.
Figure 5B:
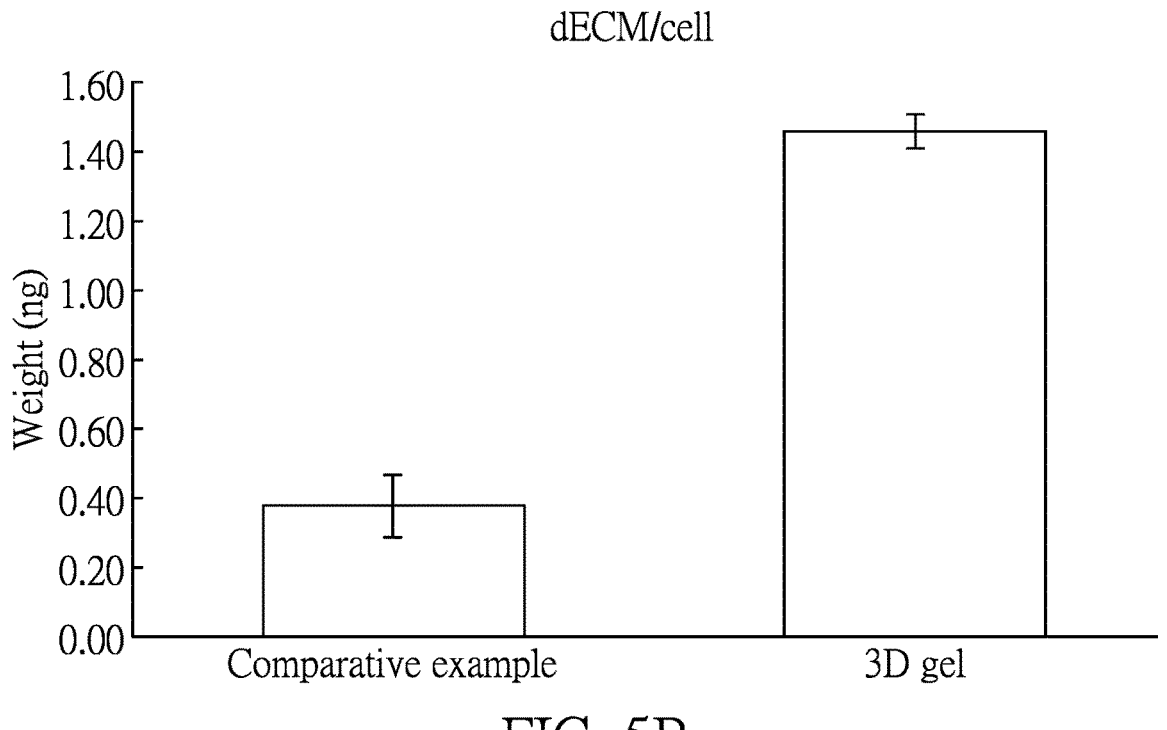
FIG. 5B is another histogram showing differences in weights of dECM/cells when cell cultures are carried out in different ways.
Figure 6:
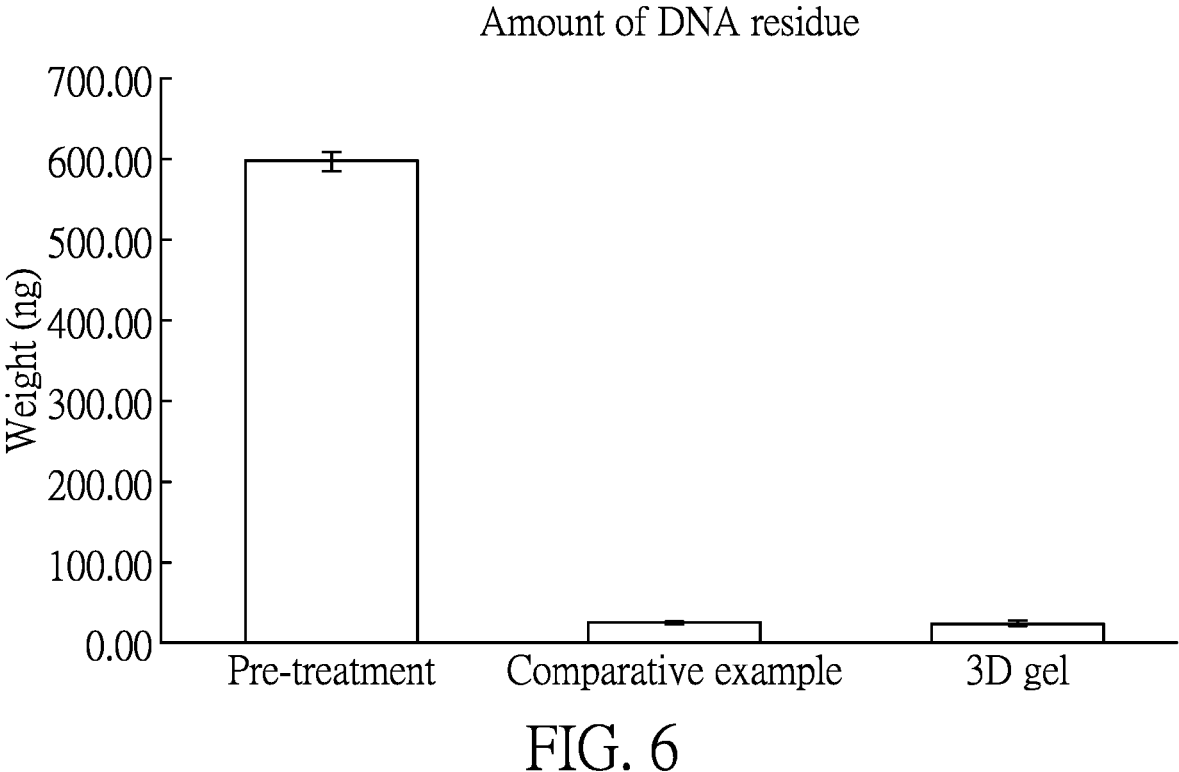
FIG. 6 is another histogram showing differences in DNA residues when cell cultures are carried out in different ways.

Referring to FIG. 5A, FIG. 5B, and FIG. 6, in one embodiment of the present disclosure, through the 3D gel manufacturing process, the gel is manufactured into micron-sized spherical structures having an average particle size of 0.4 mm. As shown in FIG. 5A and FIG. 5B, the total protein concentration of the product in this embodiment of the present disclosure is 73.24±2.64 mg, and is higher than the total protein concentration of 19.00±4.58 mg of the Comparative Example. In addition, for the average amount of dECM produced per cell, after calculation, the average amount of dECM produced per cell in this embodiment of the present disclosure is 1.46±0.05 dECM/cells (ng), which is higher than 0.38±0.09 dECM/cells (ng) as in the Comparative Example. Therefore, compared to the conventional method (i.e., the Comparative Example), the method for manufacturing an extracellular matrix composition of the present disclosure has higher single cell yield, and the 3D gel manufacturing process has better performance than the 2D gel manufacturing process. Therefore, the method for manufacturing an extracellular matrix composition of the present disclosure can effectively save operation time and obtain high yield of extracellular matrix composition.

As shown in FIG. 6, in the 3D gel manufacturing process, the yield can be further increased while maintaining excellent decellularization effect, so that the finished dECM product has almost no DNA residue.

BENEFICIAL EFFECTS OF THE EMBODIMENTS

In conclusion, in the method for manufacturing an extracellular matrix composition provided by the present disclosure, by virtue of "the crosslinking treatment including adding a crosslinking agent to the gel to obtain a crosslinked gel," and "the decrosslinking treatment including adding a decrosslinking agent to the crosslinked gel to obtain a decrosslinked mixture that contains an extracellular matrix," the yield of the extracellular matrix composition can be increased.

The method for manufacturing an extracellular matrix composition provided by the present disclosure includes steps of crosslinking and decrosslinking, so that the gel can be used to carry out cell culture in multiple forms, and the yield of the extracellular matrix composition can be further increased. In addition, the 3D gel manufacturing process provides more surface contact area than the 2D gel manufacturing process. Therefore, when the numbers of the cells are initially the same in two cell cultures, the 3D gel manufacturing process provides an improved cell growth environment that allows for a more rapid and complete cell growth, thereby further increasing the yield of the extracellular matrix composition.

Furthermore, the extracellular matrix has poor gel kinetic properties, so that the accuracy of 3D bio-printing using the extracellular matrix is limited. The present disclosure provides a method for manufacturing an extracellular matrix composition, which can produce a dECM gel having properties of a gel such as having a viscosity of from 1 cP to 100 cP, and components of the dECM gel include proteins, cytokines, growth factors, etc. Compared to the dECM solution produced by using the conventional method, the dECM gel is more suitable for manufacturing of bio-ink.

Moreover, the extracellular matrix composition of the present disclosure is manufactured from a single type cell culture, so that the extracellular matrix composition of a single type cell can be selectively obtained, thereby controlling the stability of the batch of the extracellular matrix composition that is manufactured.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A method for manufacturing an extracellular matrix composition, comprising:
providing a gel;
carrying out a crosslinking treatment, wherein the crosslinking treatment includes adding a crosslinking agent to the gel to obtain a crosslinked gel;
culturing cells of a singular type on the crosslinked gel using a culture solution to let the cells to proliferate;
carrying out a decrosslinking treatment, wherein the decrosslinking treatment includes adding a decrosslinking agent to the crosslinked gel to obtain a decrosslinked mixture that contains an extracellular matrix; and
carrying out an extraction treatment, wherein the extraction treatment includes adding a lysis enzyme to the decrosslinked mixture and filtering the decrosslinked mixture to obtain the extracellular matrix composition.

2. The method according to claim 1, wherein the gel is a sodium alginate having a concentration from 3 vol % to 5 vol %.

3. The method according to claim 1, wherein the gel is a three-dimensional gel, and the three-dimensional gel has a micron-sized spherical structure or a laminar printed structure, the micron-sized spherical structure having an average particle size ranging from 0.2 mm to 2 mm.

4. The method according to claim 1, wherein the crosslinking agent is calcium chloride, barium chloride, zinc chloride, calcium carbonate, calcium sulfate, or calcium lactate.

5. The method according to claim 1, wherein the cells are human and animal mesenchymal stem cells, human hepatocellular carcinoma cells, fibroblasts, or epithelial stem cells.

6. The method according to claim 1, wherein the culture solution includes 50 μg/ml to 100 g/ml of ascorbic acid.

7. The method according to claim 1, wherein the decrosslinking agent is sodium citrate or ethylenediaminetetraacetic acid.

8. The method according to claim 1, wherein, before carrying out the decrosslinking treatment, the method further comprises a decellularization treatment that includes adding a decellularizing agent.

9. The method according to claim 1, wherein the lysis enzyme is pepsin or collagenase, and the lysis enzyme is mixed and stirred with the decrosslinked mixture.

10. The method according to claim 1, wherein the extraction treatment includes filtering the decrosslinked mixture through a filter having a pore size of 0.22 μm.

* * * * *